May 2, 1967 D. H. MOREY, JR Plant Pat. 2,737
ROSE PLANT
Filed April 22, 1966
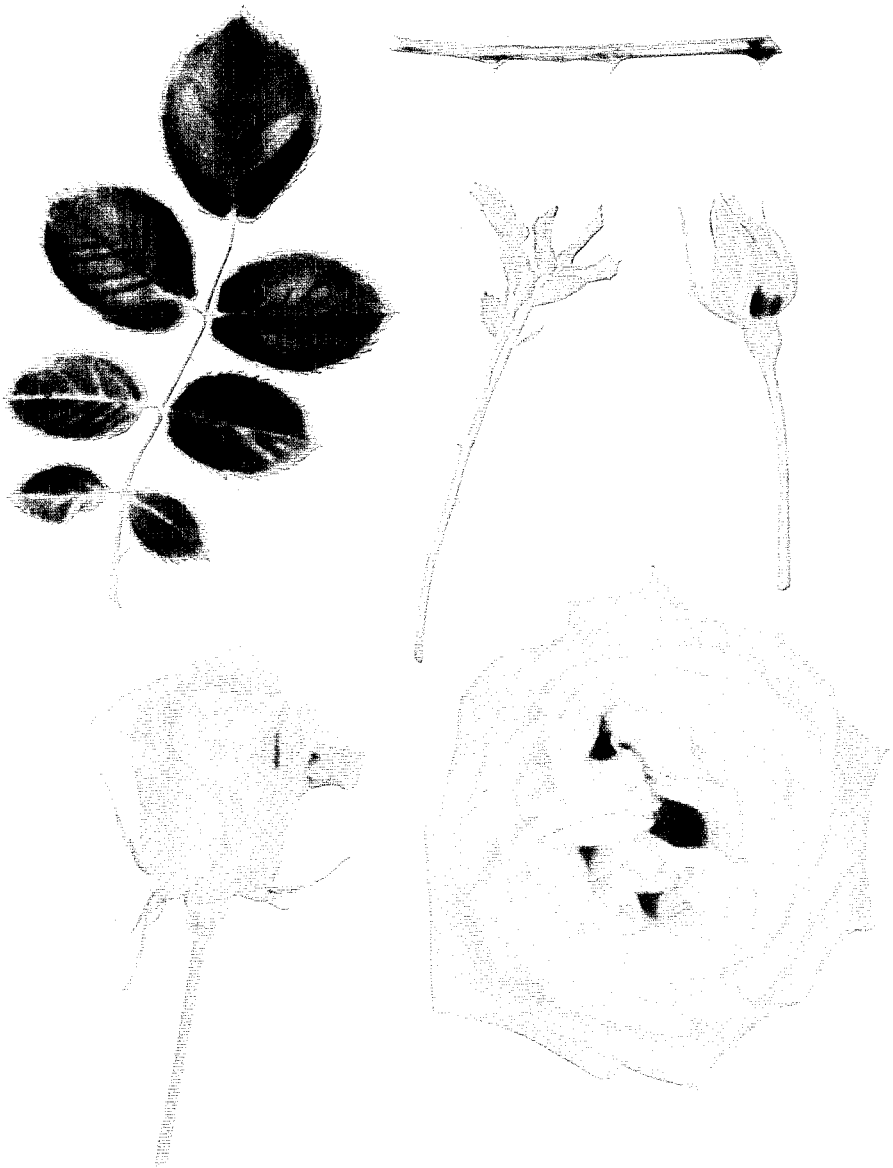
Inventor.
Dennison H. Morey, Jr.
By: Robb & Robb
Attorneys.

United States Patent Office

Plant Pat. 2,737
Patented May 2, 1967

2,737
ROSE PLANT

Dennison H. Morey, Jr., Santa Rosa, Calif., assignor to Jackson & Perkins Company, Newark, N.Y., a corporation of New York

Filed Apr. 22, 1966, Ser. No. 544,636
1 Claim. (Cl. Plt.—20)

The present invention relates to a new and distinct variety of rose plant of the hybrid tea class, which was originated by me by crossing the variety known as "Chrysler Imperial" (Plant Patent No. 1,167) with an unnamed and unpatented dark red flowered seedling of the variety known as "Zulu Queen" (Plant Patent No. 363).

The primary objective of this breeding was to produce a new hybrid tea rose variety that is free blooming in habit and produces large red flowers. This objective was fully achieved, along with other desirable features, as evidenced by the following unique combination of characteristics which are outstanding in the new variety and which distinguish it from its parents, as well as from all other varieties of which I am aware:

(1) Abundant foliage;
(2) A very free blooming habit;
(3) An urn-shaped bud form;
(4) Open flowers of large size and double form;
(5) A distinctive and attractive Scarlet-Red general color tonality of the flowers; and
(6) A strong tea flower fragrance.

Asexual reproduction of my new variety by budding, as performed at Pleasanton, Calif., and also at Newark, N.Y., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Chrysler Imperial."
*Pollen parent.*—An unnamed dark red flowered seedling of "Zulu Queen."

Classification:
*Botanic.*—Hybrid tea.
*Commercial.*—Hybrid tea.

*Flower*

(Observations made from specimens grown outdoors at Newark, N.Y., in the early morning during the latter part of the month of July.)

Blooming habit: Recurrent—continuous; very free blooming.

Bud:
*Size.*—Large.
*Form.*—Urn-shaped; is not affected by wet or hot weather.
*Color.*—When sepals first divide—Van Dyke Red, Plate 13. When petals begin to unfurl—Oxblood Red, Plate 1. When half-blown: inside of petals—Carmine, Plate 1, with center of petals lightly overcast with Nopal Red, Plate 1; reverse of petals—Nopal Red, Plate 1, lightly overcast with Spectrum Red, Plate 1.
*Sepals.*—Slightly branched; curl back when petals begin to unfurl. Color: inside—Oil Green, Plate 5; outside—Deep Dull Yellow Green (1), Plate 32.

*Calyx.*—Color—Deep Dull Yellow Green (1), Plate 32. Shape — apple. Size — Large. Aspect — smooth. Odor when rubbed—none.
*Peduncle.* — Length — long. Aspect — rough. Strength — erect; slender. Color — Light Bice Green, Plate 17.
*Opening.*—Opens up well; is not affected by adverse weather conditions.

Bloom:
*Size.*—Large. Average size when fully expanded—6 inches.
*Borne.*—Both singly and several together.
*Stems.*—Long; strong.
*Form (when first opened).* — Cupped. Permanence—retains its form to the end.
*Petalage.*—Double (full but open center). Number of petals under normal conditions—from 40 to 45.
*Color.*—Center of flower—Scarlet-Red, Plate 1, very lightly overcast with Nopal Red, Plate 1. Outer petals—Spectrum Red, Plate 1. Base of petals (aiglet)—Lemon Chrome, Plate 4. Inside of petals—Scarlet-Red, Plate 1. Reverse of petals—Nopal Red, Plate 1, very lightly overcast with Spectrum Red, Plate 1. General tonality from a distance—Scarlet-Red, Plate 1.
*Discoloration.*—General tonality at end of first day—Scarlet-Red, Plate 1, lightly overcast with Nopal Red, Plate 1. Second day—Scarlet-Red, Plate 1, slightly overcast with Nopal Red, Plate 1. Third day—Scarlet Red, Plate 1.

Petals:
*Texture.*—Leathery; is not affected by wet or hot weather.
*Appearance.*—Inside—velvety. Outside—satiny.
*Form.*—Oval.
*Arrangement.*—Imbricated (regularly arranged shingle-like).
*Petaloids in center.*—Few; large.
*Persistence.*—Drop off cleanly.
*Fragrance.*—Strong. Nature—tea (average hybrid tea scent).
*Lasting quality.*—On the plant—long. As cut flower—long.

*Genital organs*

Stamens, anthers: Medium size; many; regularly arranged around styles.
Stamens, filaments (threads): Medium length. Color—Amber Yellow, Plate 16.
Pollen: Color—Pale Ochraceous-Buff, Plate 15.
Styles: Loosely separated; uneven length; short; thin.
Stigmas: Color—Naples Yellow, Plate 16.
Ovaries: All enclosed in calyx.
Hips: None.
Seeds: None.

*Plant*

Form: Bush.
Growth: Vigorous; upright.
Foliage: Compound of 3–7 leaflets.
*Size.*—Large.
*Quantity.*—Abundant.
*Color.*—New foliage: upper side—Yellowish Oil Green, Plate 5, with outer edge of leaf overcast with Oxblood Red, Plate 1; underside—Yellowish Citrine, Plate 16, lightly overcast with Acajou Red, Plate 13. Old foliage: upper side—Varley's Green, Plate 18; under side—Light Hellebore Green, Plate 17.
*Shape.*—Oval pointed.

*Texture.*—Upper side—glossy. Under side—smooth.
*Ribs and veins.*—Ordinary.
*Edge.*—Serrated (saw toothed).
*Serration.*—Both double and single; small.
*Leaf stem.*—Color—Spinach Green, Plate 5. Under side—prickly.
*Stipules.*—Medium length; smooth.

Wood:

*New wood.*—Color—Oil Green, Plate 5. Bark—smooth.
*Old wood.*—Color—Jade Green, Plate 31. Bark—smooth.

Thorns:

*Thorns.*—Quantity: on main stalks—ordinary; on laterals from stalk—ordinary. Form—narrow base; medium length; some hooked downward and some hooked upward. Color (when young)—Begonia Rose, Plate 1. Position—irregular.

*Prickles.*—Quantity: on main stalks—none; on laterals—none.
*Short needles.*—Quantity: on main stalks—none; on laterals—none.

I claim:

A new and distinct variety of rose plant of the hybrid tea class, substantially as herein shown and described, characterized particularly as to novelty by the unique combination of abundant foliage, a very free blooming habit, an urn-shaped bud form, open flowers of large size and double form, a distinctive and attractive Scarlet-Red general color tonality of the flowers, and a strong tea flower fragrance.

No references cited.

ANTONIO F. GUIDA, *Acting Primary Examiner.*

ROBERT E. BAGWILL, ABRAHAM G. STONE, *Examiners.*